United States Patent
Kitagawa et al.

(10) Patent No.: US 10,552,945 B2
(45) Date of Patent: Feb. 4, 2020

(54) SAMPLE OBSERVATION APPARATUS AND METHOD FOR GENERATING OBSERVATION IMAGE OF SAMPLE

(71) Applicant: OLYMPUS CORPORATION, Shibuya-ku, Tokyo (JP)

(72) Inventors: Hisao Kitagawa, Tokyo (JP); Yusuke Yamashita, Tokyo (JP); Yasunari Matsukawa, Saitama (JP)

(73) Assignee: OLYMPUS CORPORATION, Tokyo (JP)

(*) Notice: Subject to any disclaimer, the term of this patent is extended or adjusted under 35 U.S.C. 154(b) by 858 days.

(21) Appl. No.: 14/728,396

(22) Filed: Jun. 2, 2015

(65) Prior Publication Data

US 2015/0371368 A1     Dec. 24, 2015

(30) Foreign Application Priority Data

Jun. 19, 2014 (JP) ................................ 2014-126228

(51) Int. Cl.
*G06T 3/40* (2006.01)
*G06T 7/00* (2017.01)
(Continued)

(52) U.S. Cl.
CPC .......... *G06T 3/4053* (2013.01); *G02B 21/008* (2013.01); *G02B 21/0072* (2013.01);
(Continued)

(58) Field of Classification Search
CPC .. G02B 21/367; G02B 27/58; G02B 21/0072; G02B 21/0076; G02B 21/008;
(Continued)

(56) References Cited

U.S. PATENT DOCUMENTS

| 5,283,433 A * | 2/1994 | Tsien ................. G02B 21/008 250/234 |
| 7,969,582 B2 * | 6/2011 | Fujii ..................... G01B 11/24 250/234 |

(Continued)

FOREIGN PATENT DOCUMENTS

| JP | 2008066978 A | 3/2008 |
| JP | 2012078408 A | 4/2012 |

(Continued)

OTHER PUBLICATIONS

Extended European Search Report dated Nov. 10, 2015, issued in counterpart European Application No. 15171381.5.

(Continued)

*Primary Examiner* — Christopher S Kelley
*Assistant Examiner* — Boubacar Abdou Tchoussou
(74) *Attorney, Agent, or Firm* — Holtz, Holtz & Volek PC

(57) ABSTRACT

A sample observation apparatus includes a memory and a main controller. The main controller stores a first number of photoelectrons required in a raw image for generating a super-resolution image. The main controller calculates the number of image data sets to be added together for generating the raw image based on the first number of photoelectrons stored in the memory and a predetermined image acquisition condition, acquires multiple sets of image data of the same region of a sample by repeatedly detecting light from the same region based on the calculated number of image data sets, and generates the raw image by adding together the acquired multiple sets of image data of the same region.

4 Claims, 11 Drawing Sheets

(51) Int. Cl.
*G02B 21/36* (2006.01)
*G02B 21/00* (2006.01)
*G02B 27/58* (2006.01)
*G01N 21/64* (2006.01)

(52) U.S. Cl.
CPC ....... *G02B 21/0076* (2013.01); *G02B 21/367* (2013.01); *G02B 27/58* (2013.01); *G06T 7/0012* (2013.01); *G01N 21/6458* (2013.01); *G06T 2207/10056* (2013.01)

(58) Field of Classification Search
CPC ................. G06T 3/4053; G06T 7/0012; G06T 2207/10056; G01N 21/6458
See application file for complete search history.

(56) References Cited

U.S. PATENT DOCUMENTS

| | | | |
|---|---|---|---|
| 8,780,192 B2 | 7/2014 | Hayashi | |
| 8,817,088 B2 | 8/2014 | Hayashi | |
| 8,933,418 B2* | 1/2015 | Hayashi | G01N 21/6458 250/458.1 |
| 9,383,563 B2* | 7/2016 | Hayashi | G02B 21/0076 |
| 9,726,877 B2* | 8/2017 | Kleppe | G02B 21/367 |
| 2008/0002030 A1 | 1/2008 | Sakurai et al. | |
| 2009/0059039 A1* | 3/2009 | Smith | H04N 5/235 348/241 |
| 2009/0153878 A1* | 6/2009 | Fujii | G01B 11/24 356/601 |
| 2009/0185760 A1* | 7/2009 | Okada | G06T 3/4069 382/299 |
| 2010/0128263 A1* | 5/2010 | Kobayashi | G01J 3/06 356/300 |
| 2010/0182683 A1* | 7/2010 | Okugawa | G02B 5/0833 359/389 |
| 2010/0207037 A1* | 8/2010 | Tearney | G01N 21/6458 250/459.1 |
| 2010/0303386 A1* | 12/2010 | Enderlein | G02B 21/367 382/299 |
| 2011/0279711 A1 | 11/2011 | Sakurai et al. | |
| 2012/0069344 A1* | 3/2012 | Liu | G01B 9/04 356/450 |
| 2012/0147205 A1* | 6/2012 | Lelescu | H04N 13/0029 348/218.1 |
| 2013/0010098 A1* | 1/2013 | Kalkbrenner | G01N 21/6428 348/79 |
| 2013/0015366 A1* | 1/2013 | Hayashi | G01N 21/6458 250/458.1 |
| 2014/0198198 A1* | 7/2014 | Geissbuehler | G01N 21/6458 348/79 |
| 2014/0361154 A1* | 12/2014 | Hayashi | G02B 21/0076 250/234 |
| 2015/0035964 A1* | 2/2015 | Kleppe | G02B 21/0076 348/79 |
| 2015/0211997 A1 | 7/2015 | Dake | |
| 2015/0363922 A1* | 12/2015 | Elliott | G06T 3/4015 382/254 |
| 2015/0371431 A1* | 12/2015 | Korb | G06T 9/00 382/113 |
| 2016/0004059 A1* | 1/2016 | Menon | G02B 21/16 359/370 |

FOREIGN PATENT DOCUMENTS

| | | |
|---|---|---|
| JP | 2013020083 A | 1/2013 |
| WO | 2008029864 A1 | 3/2008 |
| WO | 2014057998 A1 | 4/2014 |

OTHER PUBLICATIONS

Geissbuehler, et al., "Comparison between SOFI and STORM", Biomedical Optics Express, vol. 2, No. 3, Mar. 1, 2011, p. 408.
Thomann, et al., "Automatic fluorescent tag detection in 3D with super-resolution: application to the analysis of chromosome movement", Journal of Microscopy, vol. 208, No. 1, Oct. 1, 2002, pp. 49-64.
Japanese Office Action (and English translation thereof) dated Dec. 5, 2017, issued in counterpart Japanese Application No. 2014-126228.
European Office Action dated Nov. 14, 2018 issued in counterpart European Application No. 15171381.5.
Dertinger, et al., "Achieving increased resolution and more pixels with Superresolution Optical Fluctuation Imaging (SOFI)", Optics Express, vol. 18, No. 18, pp. 18875-18885. XP055010427, ISSN: 1094-4087, DOI: 10.1364/OE18.018875.

* cited by examiner

FIG. 11

| Laser \ HV | | 450V | 500V | 550V | 600V |
|---|---|---|---|---|---|
| 0.1 μw | L1 | 160 | 240 | 320 | 400 |
| | L2 | 115 | 170 | 225 | 285 |
| 1 μw | L1 | 80 | 120 | 160 | 200 |
| | L2 | 55 | 85 | 115 | 140 |
| 10 μw | L1 | 40 | 60 | 80 | 100 |
| | L2 | 28 | 42 | 56 | 71 |
| 100 μw | L1 | 20 | 30 | 40 | 50 |
| | L2 | 14 | 21 | 28 | 35 |

UPPER SECTION: IMAGE-QUALITY PRIORITY MODE (L1)
LOWER SECTION: SPEED PRIORITY MODE (L2)

SAMPLE OBSERVATION APPARATUS AND METHOD FOR GENERATING OBSERVATION IMAGE OF SAMPLE

CROSS-REFERENCE TO RELATED APPLICATIONS

This application is based on Japanese Patent Application No. 2014-126228, the contents of which are incorporated herein by reference.

TECHNICAL FIELD

The present invention relates to sample observation apparatuses and to methods for generating observation images of samples.

BACKGROUND ART

Since the decoding of the human genome, the mechanism of diseases, such as cancer, and the mechanism of generation/differentiation of organs, such as the heart and cranial nerves, are being clarified at the molecular level. When observing a biological sample, such as cells, by using a microscope, it is required to observe the behavior of, for example, protein and DNA/RNA (deoxyribonucleic acid/ribonucleic acid) at the molecular level. Therefore, the importance of observation of super-resolution images that exceed optical resolution is increasing more and more.

In the related art, there are known sample observation apparatuses that function as super-resolution observation apparatuses that perform an image computational process on image data of a sample, serving as a raw image, so as to emphasize high-frequency components of the image data, thereby generating a super-resolution image in which super-resolution components are visualized (for example, see Patent Literature 1 and Patent Literature 2).

CITATION LIST

Patent Literature

{PTL 1}
Japanese Unexamined Patent Application, Publication No. 2012-78408
{PTL 2}
Japanese Unexamined Patent Application, Publication No. 2013-20083

SUMMARY OF INVENTION

In the sample observation apparatuses discussed in Patent Literature 1 and Patent Literature 2, the high-frequency components cannot be efficiently emphasized if the proportion of the high-frequency components in the image data serving as a raw image is low, and a good super-resolution image cannot be generated.

The present invention provides a sample observation apparatus that can generate a good super-resolution image while eliminating a troublesome task necessary for generating a raw image.

A first aspect of the present invention provides a sample observation apparatus including a storage section that stores information about an S/N ratio required in a raw image for generating a super-resolution image; a number-of-image-data-sets calculator that calculates a number of image data sets to be added together for generating the raw image based on the S/N-ratio information stored in the storage section and a predetermined image acquisition condition; an image-data acquisition section that acquires the image data by detecting light from a sample with the predetermined image acquisition condition; a controller that causes the image-data acquisition section to acquire multiple sets of the image data of the same region of the sample by making the image-data acquisition section repeatedly detect light from the same region based on the number calculated by the number-of-image-data-sets calculator; and a raw-image generator that adds together the multiple sets of image data of the same region acquired by the image-data acquisition section so as to generate the raw image.

According to this aspect, the controller causes the image-data acquisition section to acquire multiple sets of the image data of the same region of the sample by making the image-data acquisition section repeatedly detect light from the same region, and the raw-image generator adds together these multiple sets of image data of the same region so as to generate the raw image. Thus, even when noise becomes superimposed on the image data due to an inability to obtain a sufficient light level from the same region of the sample in a single image acquisition process, the luminance is increased in accordance with the added number of image data sets so that a raw image with a high proportion of high-frequency components and in which noise is smoothed is generated. Therefore, by performing image computational processing on the raw image to emphasize high-frequency components, a good super-resolution image in which super-resolution components are visualized can be generated.

The super-resolution effect obtained by emphasizing high-frequency components cannot be achieved unless the S/N ratio of the raw image is sufficiently high. Therefore, if the S/N ratio of the raw image decreases in accordance with the image acquisition condition, the number of image data sets to be added together needs to be increased in order to ensure a sufficient S/N ratio. Thus, in order to acquire a raw image with a high proportion of high-frequency components and in which noise is smoothed, it is necessary to adjust the optimal combination of the image acquisition condition and the number of image data sets to be added together.

In this aspect, the number-of-image-data-sets calculator calculates the number of image data sets to be added together for generating the raw image based on the S/N-ratio information required in the raw image and the predetermined image acquisition condition, so that the number of image data sets required when employing the predetermined image acquisition condition can be readily ascertained. Consequently, a good super-resolution image can be generated, while eliminating a troublesome task necessary for generating a raw image.

In the above aspect, the S/N-ratio information may include a first number of photoelectrons, which is the number of photoelectrons per pixel required for obtaining a desired S/N ratio in the raw image. The number-of-image-data-sets calculator may divide the first number of photoelectrons by a second number of photoelectrons, which is the number of photoelectrons per pixel in the image data acquired with the predetermined image acquisition condition by the image-data acquisition section.

In a detector, such as a photomultiplier tube (PMT) that detects light, serving as the image-data acquisition section, if the HV (high voltage) multiplication gain serving as an image acquisition condition is too high, an electric signal per photoelectron becomes large, resulting in saturation of the electric signal with a small number of photoelectrons. Therefore, the number of photoelectrons that can be detected in a single image acquisition process decreases, and a desired noise smoothing effect cannot be achieved unless the number of image data sets to be added together is increased.

In this case, because the number of photoelectrons is equivalent to the square of the S/N ratio, the first number of photoelectrons is determined from, for example, a preliminary experiment. The second number of photoelectrons is determined based on luminance information of image data acquired in advance by the image-data acquisition section with the predetermined image acquisition condition and also based on that image acquisition condition. Therefore, by simply determining the first number of photoelectrons and the second number of photoelectrons in advance, the required number of image data sets can be readily ascertained, and a troublesome task necessary for generating a raw image can be eliminated.

In the above aspect, the sample observation apparatus may further include an input section that allows a user to input whether or not to additionally add the image data based on the raw image generated by the raw-image generator. When an input indicating that the image data is to be additionally added is received by the input section, the controller may make the image-data acquisition section continue acquiring the image data for the same region of the sample.

In a sample, for example, there may be factors that are actually difficult to predict, such as degradation or photochemical fading of fluorescent molecules that label biomolecules. By allowing the user to determine whether or not image data is to be additionally added based on an actual raw image, a raw image that is more appropriate for the sample can be acquired.

A second aspect of the present invention provides a sample observation apparatus including an image-data acquisition section that acquires image data by detecting light from a sample; a storage section that stores first S/N-ratio information required in a raw image for generating a super-resolution image; an S/N-ratio information calculator that calculates second S/N-ratio information to be acquired in multiple sets of the image data to be added together for generating the raw image based on the first S/N-ratio information stored in the storage section and a predetermined image acquisition time; a condition setting section that sets an image acquisition condition for acquiring the image data that satisfies the second S/N-ratio information calculated by the S/N-ratio information calculator; a controller that causes the image-data acquisition section to acquire multiple sets of image data of the same region of the sample by making the image-data acquisition section repeatedly detect light from the same region within the predetermined image acquisition time based on the image acquisition condition set by the condition setting section; and a raw-image generator that adds together the multiple sets of image data of the same region acquired by the image-data acquisition section so as to generate the raw image.

According to this aspect, the multiple sets of image data obtained as a result of the controller causing the image-data acquisition section to repeatedly detect light from the same region of the sample are added together by the raw-image generator, so that a raw image with a high proportion of high-frequency components and in which noise is smoothed is generated with respect to the same region of the sample.

If the number of times image data of the same region is repeatedly acquired is limited in accordance with the state of the sample and an experimental program, the image acquisition condition has to be adjusted in order to ensure a sufficient S/N ratio.

In this aspect, the S/N-ratio information calculator calculates the second S/N-ratio information to be acquired in multiple sets of the image data obtained within the predetermined image acquisition time for generating the raw image, and the condition setting section sets the image acquisition condition for acquiring image data that satisfies the second S/N-ratio information, so that the image acquisition condition required when the image acquisition time is limited can be readily ascertained. Consequently, a good super-resolution image can be generated, while eliminating a troublesome task necessary for generating a raw image.

In the above aspect, the first S/N-ratio information may include a first number of photoelectrons, which is the number of photoelectrons per pixel required for obtaining a desired S/N ratio in the raw image. The S/N-ratio information calculator may divide the first number of photoelectrons by the number of times the image data is repeatedly acquirable within the predetermined image acquisition time so as to calculate a second number of photoelectrons as the second S/N-ratio information, the second number of photoelectrons being the number of photoelectrons per pixel in each set of the image data. The condition setting section may set the image acquisition condition such that desired luminance is obtained when a third number of photoelectrons, which is the number of photoelectrons per pixel in the image data acquired by the image-data acquisition section, satisfies the second number of photoelectrons.

With this configuration, by simply determining the first number of photoelectrons and the second number of photoelectrons in advance from, for example, a preliminary experiment, the image acquisition condition required when the image acquisition time is limited can be readily ascertained, and a troublesome task necessary for generating a raw image can be eliminated.

In the above aspect, one or more of an image processing algorithm of a filter that emphasizes a high-frequency component of the raw image, a detection gain of the image-data acquisition section, an intensity of laser light to be radiated onto the sample, a method for acquiring the image data, and a method for adding together the image data may individually include a single applicable option or multiple applicable options and may be employable by being arbitrarily combined by a user.

According to this configuration, with a desired combination selected by the user in accordance with the purpose of the experiment, a troublesome task necessary for generating a raw image can be eliminated.

In the above aspect, multiple combinations of one or more of an image processing algorithm of a filter that emphasizes a high-frequency component of the raw image, a detection gain of the image-data acquisition section, an intensity of laser light to be radiated onto the sample, a method for acquiring the image data, and a method for adding the image data sets may be applicable and may be employable by allowing a user to arbitrarily select any one of the combinations.

According to this configuration, with a simple process performed by the user, which simply involves selecting any one of the preset combinations, a troublesome task necessary for generating a raw image can be eliminated.

A third aspect of the present invention provides a method for generating an observation image of a sample. The method causes a controller to perform a process including executing control for causing an image-data acquisition section, which acquires image data by detecting light from the sample, to repeatedly acquire image data of the same region of the sample multiple times, and generating a raw image for creating a super-resolution image of the sample by adding together multiple sets of the image data of the same region repeatedly acquired by the image-data acquisition section as a result of the control. The method includes causing the controller to store in advance information related to an S/N ratio that the raw image should have; causing the controller to execute control for determining the number of the image data sets to be added together for generating the raw image based on a preset image acquisition condition for the image-data acquisition section and the stored information related to the S/N ratio and repeatedly acquiring the image data of the same region in accordance with the determined number, or control for determining information related to an S/N ratio that the image data acquired by the image-data acquisition section should have based on a preset image acquisition time and the stored information related to the S/N ratio and making the image-data acquisition section repeatedly acquire the image data of the same region within the image acquisition time in a state where an image acquisition condition for acquiring the image data, which satisfies the determined information related to the S/N ratio, is set in the image-data acquisition section; and causing the controller to execute a process for generating the raw image by adding together multiple sets of the image data of the same region acquired by the image-data acquisition section as a result of the control.

The present invention is advantageous in that a good super-resolution image can be generated, while eliminating a troublesome task necessary for generating a raw image.

BRIEF DESCRIPTION OF DRAWINGS

FIG. 11 illustrates an example of a table used for determining the number of averaging scan lines from HV and laser intensity.

DESCRIPTION OF EMBODIMENTS

First Embodiment

Figure 1:
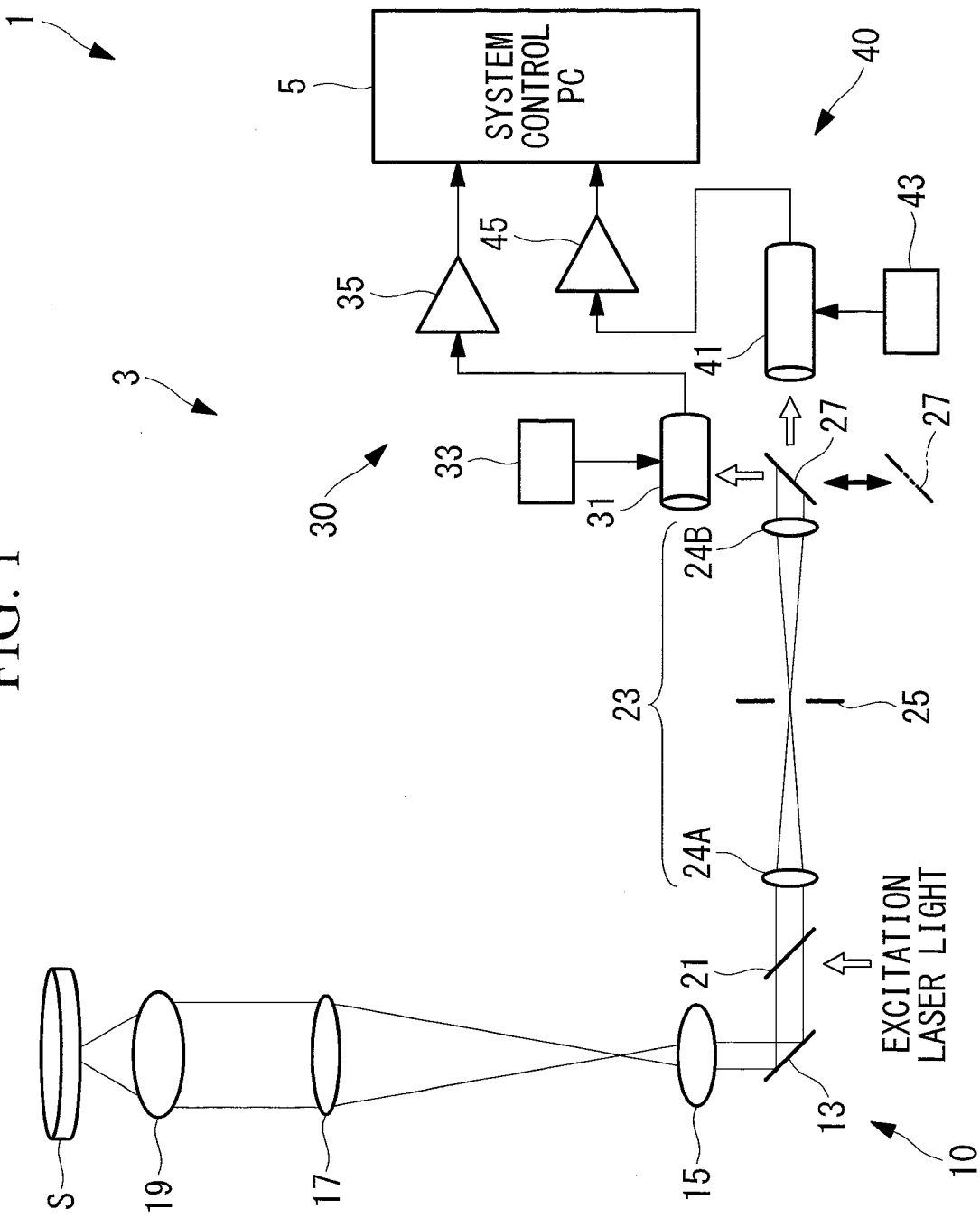
FIG. 1 schematically illustrates the configuration of a sample observation apparatus according to a first embodiment of the present invention.

A sample observation apparatus and a method for generating an observation image of a sample according to a first embodiment of the present invention will be described below with reference to the drawings.

As shown in FIGS. 1 to 5, a sample observation apparatus 1 according to this embodiment includes a scanning laser microscope 3 and a system control PC (personal computer) 5 that performs, for example, control of the scanning laser microscope 3.

The scanning laser microscope 3 includes a microscope body 10 that radiates excitation laser light onto a sample S, such as biological cellular tissue, and a first detection unit 30 and a second detection unit 40 that acquire light intensity signals by detecting fluorescence collected from the sample S irradiated with the excitation laser light from the microscope body 10.

The microscope body 10 includes a stage 11 (see FIGS. 3 to 5) on which the sample S is placed, a light source (not shown) that generates excitation laser light, a scanner (scanning section) 13 that scans the excitation laser light emitted from the light source, a pupil projection lens 15 that condenses the excitation laser light scanned by the scanner 13, an imaging lens 17 that converts the excitation laser light condensed by the pupil projection lens 15 into collimated light, and an objective lens 19 that radiates the excitation laser light converted into collimated light onto the sample S and that collects fluorescence generated in the sample S.

The microscope body 10 further includes a dichroic mirror 21 that splits off the fluorescence (return light) collected by the objective lens 19 and returning along the optical path of the excitation laser light via the imaging lens 17, the pupil projection lens 15, and the scanner 13 from the optical path, a relay lens 23 that relays the fluorescence split off by the dichroic mirror 21, a diaphragm 25 having an opening at an optically conjugate position with respect to the focal position of the objective lens 19, and an optical-path switching mirror 27 that switches the optical path of the fluorescence relayed by the relay lens 23.

Figure 3:
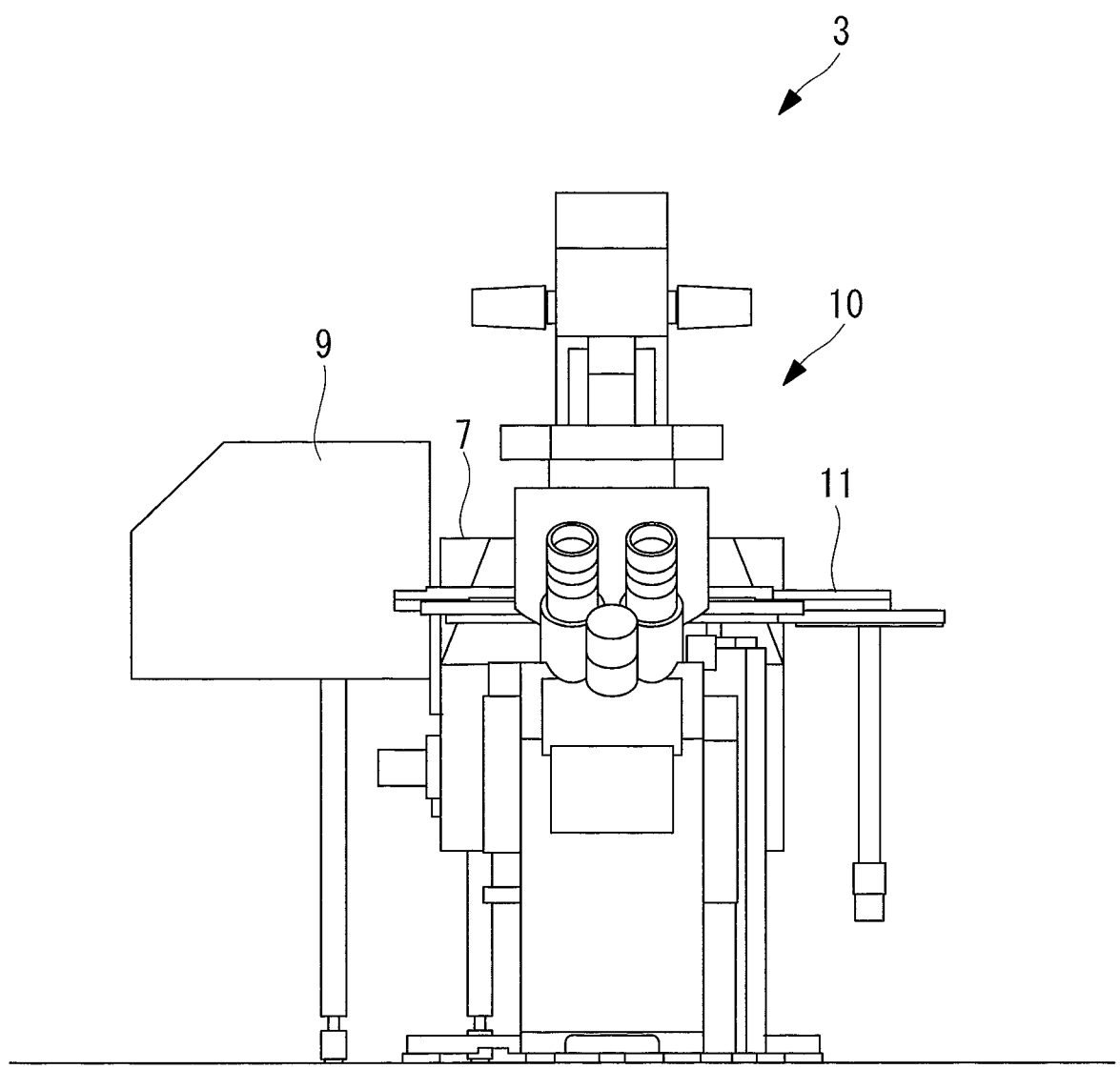
FIG. 3 is a front view of a scanning laser microscope in FIG. 1.
Figure 4:
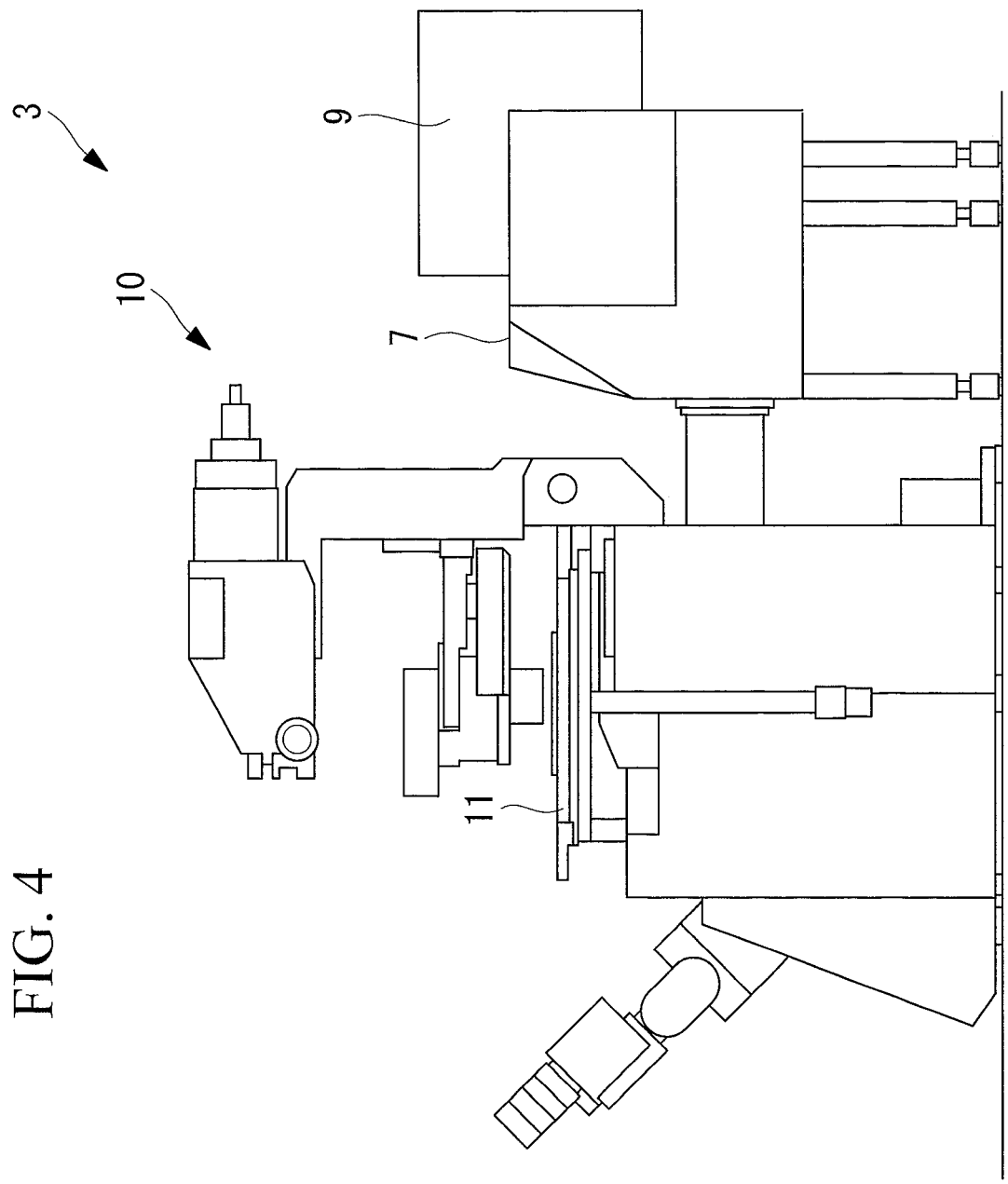
FIG. 4 is a side view of the scanning laser microscope in FIG. 3.
Figure 5:
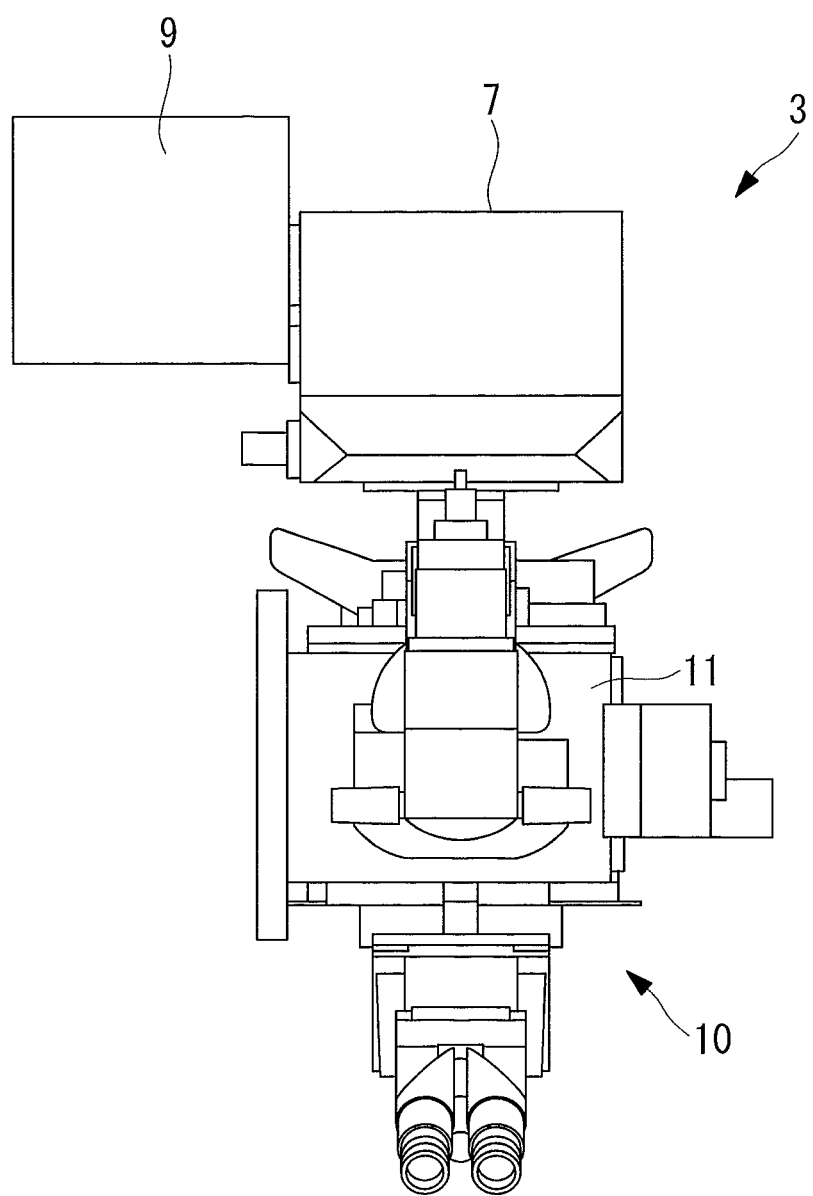
FIG. 5 is a top view of the scanning laser microscope in FIG. 3.

The scanner 13 is accommodated in a scanning unit (SU) 7 shown in FIGS. 3 to 5. The scanner 13 includes two galvanometer mirrors (not shown), which are disposed facing each other and are swivelable about axes that are orthogonal to each other. The scanner 13 deflects the excitation laser light by swiveling the two galvanometer mirrors so as to be capable of scanning the excitation laser light two-dimensionally (X-axis direction and Y-axis direction) on the sample S.

The swiveling speed of one of the galvanometer mirrors is set to be sufficiently higher than the swiveling speed of the other galvanometer mirror. The higher-speed galvanometer mirror is used for scanning on the sample S in the main scanning direction (X-axis direction), whereas the lower-speed galvanometer mirror is used for shifting a scan position on the sample S in the sub-scanning direction (Y-axis direction). These two galvanometer mirrors are swiveled about their axes by a motor (not shown).

The dichroic mirror 21 reflects the excitation laser light from the light source toward the scanner 13 and transmits the fluorescence from the sample S toward the relay lens 23.

The relay lens 23 is constituted of a confocal lens 24A that focuses the fluorescence transmitted through the dichroic mirror 21 and projects a fluorescence spot onto the aperture position of the diaphragm 25, and an imaging lens 24B that images the fluorescence projected by the confocal lens 24A.

The aperture diameter of the diaphragm 25 is changeable by the system control PC 5. In this embodiment, the diaphragm 25 has an aperture diameter that is smaller than the diameter of the fluorescence spot projected by the confocal lens 24A, that is, a confocal spot. For example, the aperture diameter is set to be about ½ of the diameter of the confocal spot.

The optical-path switching mirror 27 is disposed so as to be insertable into and removable from the optical path of the fluorescence relayed by the relay lens 23. When inserted into the optical path of the fluorescence, the optical-path switching mirror 27 reflects the fluorescence from the relay lens 23 toward the first detection unit 30. When the optical-path switching mirror 27 is removed from the optical path of the fluorescence, the fluorescence from the relay lens 23 can directly enter the second detection unit 40.

The first detection unit 30 is contained within the scanning unit 7. The first detection unit 30 includes a multi-alkali PMT (photo-multiplier tube, image-data acquisition section) 31 that detects the fluorescence and outputs a light intensity signal with a magnitude according to the light level of the fluorescence, a first HV power supply 33 that applies an HV (high voltage, applied voltage) to the multi-alkali PMT 31, and a first amplifier 35 that amplifies the light intensity signal output from the multi-alkali PMT 31.

The multi-alkali PMT 31 is a side-on-type PMT and includes a multi-alkali photoelectric surface (not shown) that receives the fluorescence and performs photoelectric conversion thereof.

The second detection unit 40 is accommodated in a high-sensitivity detection unit (HSD: high sensitivity detector) 9 shown in FIGS. 3 to 5. The second detection unit 40 includes a GaAsP-PMT (gallium arsenide phosphide PMT, image-data acquisition section) 41 that detects the fluorescence and outputs a light intensity signal with a magnitude according to the light level of the fluorescence, a second HV power supply 43 that applies an HV to the GaAsP-PMT 41, and a second amplifier 45 that amplifies the light intensity signal output from the GaAsP-PMT 41.

The GaAsP-PMT 41 is a head-on-type PMT and includes a photoelectric surface (not shown) that uses a GaAsP compound. The GaAsP-PMT 41 has higher sensitivity than the multi-alkali PMT 31 and produces image data with low noise.

Figure 2:
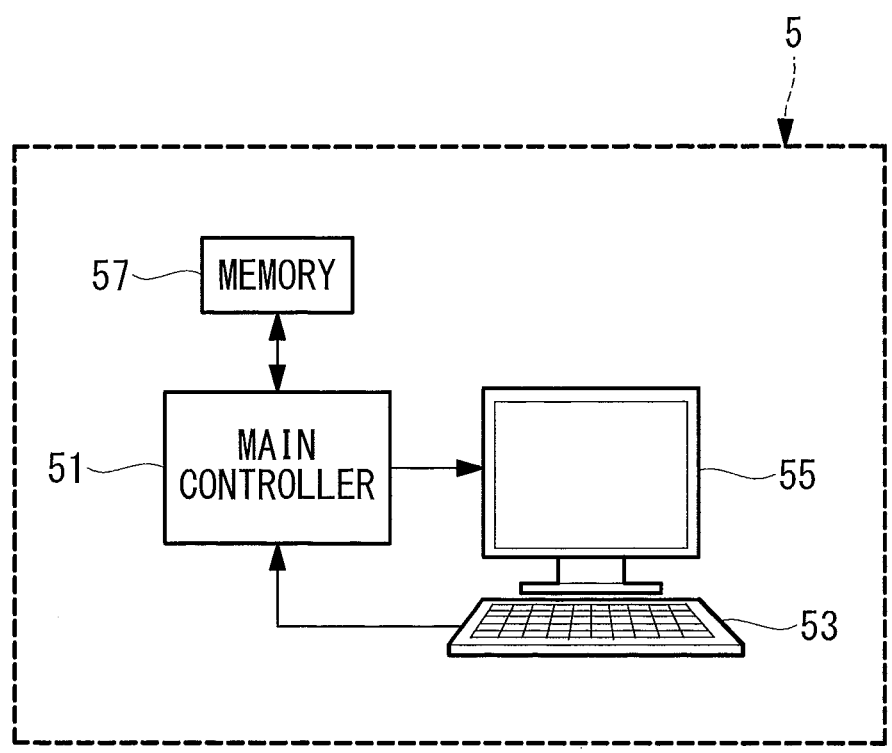
FIG. 2 schematically illustrates the configuration of a system control PC in FIG. 1.

As shown in FIG. 2, the system control PC 5 includes a main controller (image-data acquisition section, number-of-image-data-sets calculator, controller, raw-image generator) 51 that performs configuration of the apparatus, acquisition and processing of image data, and so on; an input device (input section) 53, such as a mouse or a keyboard, with which a user inputs a command to the main controller 51; a monitor 55 such as an LCD (liquid crystal display) that displays, for example, an image of the sample S; and a memory (storage section) 57 that stores an apparatus parameter A (S/N-ratio information) related to a desired S/N ratio required in a raw image for creating a super-resolution image.

The number of photoelectrons per pixel required for obtaining the desired S/N ratio in the aforementioned raw image is preliminarily stored as the apparatus parameter A in the memory 57. The number of photoelectrons per pixel required for obtaining the desired S/N ratio in the raw image will be referred to as "first number of photoelectrons" hereinafter. Because the number of photoelectrons is equivalent to the square of the S/N ratio, the S/N ratio required in the raw image can be determined from, for example, a preliminary experiment, and the first number of photoelectrons can be calculated by raising the determined S/N ratio to the second power.

In accordance with the command input to the input section 53 by the user, the main controller 51, for example, sets the scanning conditions of the scanner 13, sets the aperture diameter of the diaphragm 25, inserts or removes the optical-path switching mirror 27, sets the amplification gain of the first amplifier 35 and the second amplifier 45, and sets the HV of the first HV power supply 33 and the second HV power supply 43.

Furthermore, the main controller 51 controls the scanner 13 and also acquires image data of the sample S by converting the light intensity signal transmitted from the first amplifier 35 or the second amplifier 45 into luminance information for each pixel corresponding to the scan position of the scanner 13. Moreover, the main controller 51 displays the acquired image data on the monitor 55.

Furthermore, based on predetermined image acquisition conditions, such as the first number of photoelectrons (apparatus parameter A) required in the raw image and stored in the memory 57, HV multiplication gain, and circuit gain, the main controller 51 calculates the number of image data sets to be added together for generating the raw image, that is, the number of additions of image data sets.

Specifically, as an image parameter B, the main controller 51 calculates the number of photoelectrons per pixel in image data acquired in predetermined image acquisition conditions. The number of photoelectrons per pixel in image data acquired in predetermined image acquisition conditions will be referred to as "second number of photoelectrons" hereinafter. Then, the main controller 51 divides the first number of photoelectrons required in the raw image by the calculated second number of photoelectrons so as to calculate the number of additions of image data sets. The number of additions of image data sets will be referred to as "number of repetitions N" hereinafter.

The second number of photoelectrons can be determined based on luminance information of a pixel with a representative brightness (e.g., a maximum luminance or an intermediate luminance) in image data acquired in advance by the user in the predetermined image acquisition conditions and also based on those image acquisition conditions.

More specifically, the predetermined image acquisition conditions include, for example, the HV multiplication gain of the multi-alkali PMT 31 and the GaAsP-PMT 41, the current-voltage (I-V) conversion characteristics of detection circuits, the gain of the light-intensity-signal amplifiers or analog integrating circuits, and the laser light intensity of the light source.

Furthermore, the main controller 51 uses the scanner 13 and the detection units 30 and 40 to repeatedly detect the fluorescence from the same region of the sample S for the calculated number of repetitions N so as to acquire image data of the same region. For example, the main controller 51 uses the higher-speed galvanometer mirror of the scanner 13 to scan the excitation laser light N times along the same scan line in the main scanning direction and then swivels the lower-speed galvanometer mirror so as to repeat the operation for moving the scan line in the main scanning direction to the next scan line, thereby acquiring N times worth of image data for every single scan line.

Furthermore, the main controller 51 adds together N times worth of image data acquired from every single region of the sample S so as to generate the raw image. Then, the main controller 51 applies a filter that emphasizes high-frequency components to the generated raw image so as to generate a super-resolution image that exceeds the optical resolution.

The method for generating an observation image of a sample according to this embodiment involves causing the main controller (controller) 51 to perform a process including executing control for repeatedly acquiring image data of the same region of the sample S multiple times, and adding together the multiple sets of image data of the same region of the sample S repeatedly acquired as a result of this control so as to generate a raw image for creating a super-resolution image of the sample S. Specifically, the main controller 51 first stores the apparatus parameter A that the raw image should have (information related to the S/N ratio that the raw image should have) into the memory 57 in advance. Then, based on preset image acquisition conditions and the information related to the apparatus parameter A stored in the memory 57, the main controller 51 is made to determine the number of image data sets to be added together for generating the raw image and to perform control for repeatedly acquiring the determined number of image data sets of the same region of the sample S. Moreover, the main controller 51 is made to execute a process for adding together the multiple sets of image data of the same region of the sample S acquired as a result of this control so as to generate the raw image.

The operation of the sample observation apparatus 1 having this configuration and the method for generating an observation image of a sample will now be described.

When the sample observation apparatus 1 according to this embodiment is to acquire image data of the sample S by using the multi-alkali PMT 31, the main controller 51 sets the HV gain of the first HV power supply 33 and the amplifier gain of the first amplifier 35. Then, the main controller 51 inserts the optical-path switching mirror 27 into the optical path of fluorescence and causes the light source to generate excitation laser light.

The excitation laser light emitted from the light source is reflected by the dichroic mirror 21, is subsequently deflected by the scanner 13, is collected by the pupil projection lens 15, is converted into collimated light by the imaging lens 17, and is radiated onto the sample S by the objective lens 19. Thus, the excitation laser light is two-dimensionally scanned on the sample S in accordance with the swiveling motion of the scanner 13.

Fluorescence generated in the sample S as a result of being irradiated with the excitation laser light is collected by the objective lens 19, returns along the optical path of the excitation laser light via the imaging lens 17, the pupil projection lens 15, and the scanner 13, and is transmitted through the dichroic mirror 21 so as to be split off from the optical path. The fluorescence transmitted through the dichroic mirror 21 is relayed by the relay lens 23 and passes through the diaphragm 25, and is then reflected by the optical-path switching mirror 27 so as to enter the first detection unit 30.

In the first detection unit 30, the multi-alkali PMT 31 detects the fluorescence and outputs a light intensity signal with a magnitude according to the level of the detected fluorescence. The light intensity signal output from the multi-alkali PMT 31 is amplified by the first amplifier 35 and is sent to the main controller 51 of the system control PC 5.

In the main controller 51, the input light intensity signal is converted into luminance information for each pixel corresponding to the scan position of the scanner 13, so that image data of the sample S is acquired. The acquired image data is displayed on the monitor 55.

Next, in a case where image data of the sample S is to be acquired by using the GaAsP-PMT 41, the main controller 51 sets the HV gain of the second HV power supply 43 and the amplifier gain of the second amplifier 45. Then, the main controller 51 removes the optical-path switching mirror 27 from the optical path of fluorescence, and excitation laser light is scanned on the sample S by the microscope body 10 in a manner similar to the case where the multi-alkali PMT 31 is used.

The fluorescence generated in the sample S is collected by the objective lens 19, returns along the optical path of the excitation laser light, is transmitted through the dichroic mirror 21, is relayed by the relay lens 23, and subsequently enters the second detection unit 40 without traveling via the optical-path switching mirror 27.

In the second detection unit 40, the GaAsP-PMT 41 detects the fluorescence and outputs a light intensity signal. The light intensity signal is amplified by the second amplifier 45 and is sent to the main controller 51. Then, the main controller 51 acquires image data of the sample S based on the light intensity signal. The acquired image data is displayed on the monitor 55.

Figure 6:
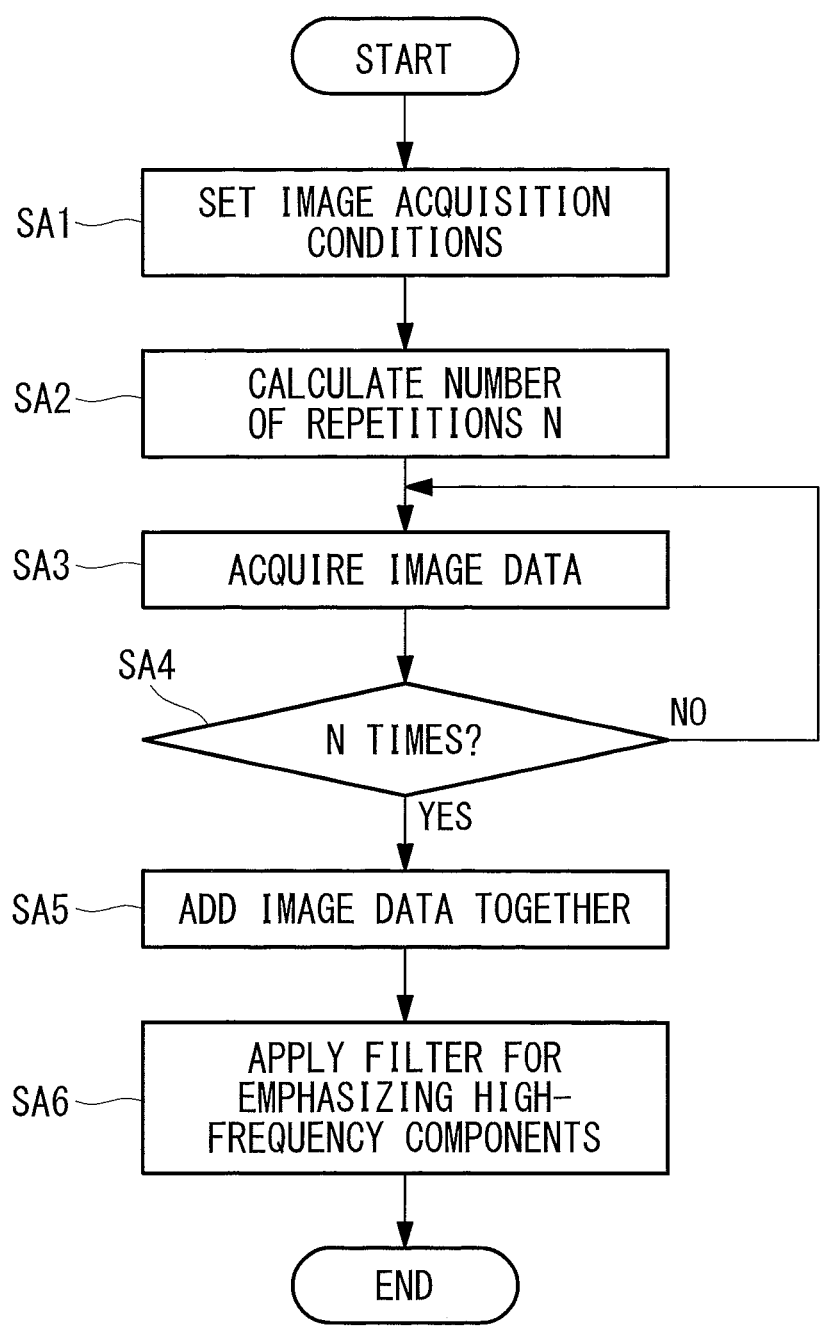
FIG. 6 is a flowchart illustrating a process performed by the sample observation apparatus in FIG. 1 for generating a super-resolution image.

The following description, with reference to the flowchart in FIG. 6, relates to a case where a super-resolution image is generated.

When a super-resolution image is to be generated by the sample observation apparatus 1 according to this embodiment, it is preferable that the above-described raw image be generated by using the GaAsP-PMT 41 having low noise included in the image data.

First, in the sample observation apparatus 1 according to this embodiment, the number of photoelectrons multiplied by the multiplication gain (HV dependency) is calculated based on the HV multiplication gain serving as a PMT parameter, the amplification gain (or integration gain) serving as a circuit parameter, and a sampling period, and an electric charge (current) per photoelectron and a luminance data increment (average value) per photoelectron are preliminarily determined.

Then, the main controller 51 sets predetermined image acquisition conditions including the HV to be applied to the GaAsP-PMT 41 and the scanning time, and adjusts the laser intensity of the light source (step SA1).

Subsequently, image data is acquired with the set image acquisition conditions, and the main controller 51 calculates the second number of photoelectrons (image parameter B) per pixel in the acquired image data.

Then, the main controller 51 reads the first number of photoelectrons (apparatus parameter A) per pixel required in the raw image from the memory 57, divides the first number of photoelectrons by the second number of photoelectrons, and calculates the number of additions of image data sets (number of repetitions N) (step SA2).

Subsequently, excitation laser light is generated by the light source, and the main controller 51 controls the scanner 13 to repeatedly scan the laser light along the same scan line in the main scanning direction, thereby acquiring multiple sets of image data of the same scan line (step SA3).

The main controller 51 determines whether or not the image data have been acquired N times from the same scan line in the sample S (step SA4) and moves to the next scan line if it is determined that the image data have been acquired N times. Thus, N times worth of image data are acquired from every scan line.

Subsequently, the main controller 51 adds together N times worth of image data for every single region of the sample S so as to generate the raw image (step SA5) and displays it on the monitor 55.

If cells with fluorescence-labeled biomolecules, such as biological cellular tissue, are to be observed as the sample S, a sufficient detection light level is not obtained by simply scanning the excitation laser light once, often resulting in acquisition of image data with rough noise (random noise)

superimposed thereon. When a process for emphasizing high-frequency components is performed on such image data by using the image data as a raw image, a good super-resolution image cannot be obtained since the noise is emphasized in the image.

In contrast, in this embodiment, the main controller 51 adds together the multiple sets of image data repeatedly acquired from the same region of the sample S, so that the luminance is increased according to the added number of image data sets with respect to the same region of the sample S, whereby a raw image with a high proportion of high-frequency components and in which noise is smoothed can be acquired.

Subsequently, the main controller 51 applies a filter that emphasizes the high-frequency components to the generated raw image so as to generate a super-resolution image in which super-resolution components are visualized (step SA6). The generated super-resolution image is displayed on the monitor 55.

In this case, if the HV multiplication gain serving as an image acquisition condition is too high in a detector like a PMT, the electric signal per photoelectron becomes large, resulting in saturation of the electric signal with a small number of photoelectrons. Therefore, the number of photoelectrons that can be detected in a single image acquisition process decreases, and a desired noise smoothing effect cannot be achieved unless the number of image data sets to be added together is increased. Consequently, in order to smooth noise and acquire a raw image with a high proportion of high-frequency components, it is necessary to adjust the optimal combination of the image acquisition conditions and the number of image data sets to be added together.

In the sample observation apparatus 1 and the method for generating an observation image of a sample according to this embodiment, the main controller 51 calculates the number of image data sets to be added together (number of repetitions N) for generating a raw image based on the first number of photoelectrons (apparatus parameter A) per pixel required for obtaining a desired S/N ratio in the raw image and the predetermined image acquisition conditions, so that the number of image data sets required when employing the predetermined image acquisition conditions can be readily ascertained. Consequently, a good super-resolution image can be generated, while eliminating a troublesome task necessary for generating a raw image.

Furthermore, since multiple sets of image data are acquired by repeatedly scanning excitation laser light along the same scan line in the main scanning direction, it is not necessary to continuously radiate the excitation laser light onto a single spot of biological cellular tissue serving as the sample S, so that the occurrence of photo-toxicity or fluorescence saturation can be prevented. Furthermore, the time intervals taken for repeatedly scanning over the same region is prevented from being excessively long, so that aging of cells as well as the influence of temperature drift of the apparatus can be reduced.

Furthermore, by setting the aperture diameter of the diaphragm 25 to about ½ of the diameter of the confocal spot, only the central beam portion of the fluorescence relayed by the relay lens 23 passes through the diaphragm 25, whereas the remaining portion is blocked by the diaphragm 25. Thus, the fluorescence at and near the peak of the center of the confocal spot is detected, so that an appropriate proportion of high-frequency components is included, and detection loss is also reduced.

In this embodiment, the main controller 51 performs acquisition of image data, calculation of the number of image data sets to be added together, acquisition of multiple sets of image data from the same region of the sample S, and processing for adding together the multiple sets of image data. Alternatively, for example, the system control PC 5 may include an image-data acquisition section that acquires image data, a number-of-image-data-sets calculator that calculates the number of image data sets to be added together, a controller that causes the image-data acquisition section to acquire multiple sets of image data from the same region of the sample S, and an image-data adding section that adds together the multiple sets of image data of the same region.

Furthermore, this embodiment can be modified as follows.

Specifically, the user is allowed to determine whether or not to additionally add image data to a temporarily-generated raw image. If image data is to be additionally added, the acquisition of image data from the same region of the sample S may be continued.

In this case, at the stage when the main controller 51 generates the raw image by adding together N times worth of image data of the same region, the raw image and a message indicating whether or not to additionally add image data may be displayed on the monitor 55. Moreover, the user may be allowed to input a command indicating whether or not to further additionally add image data into the input device (input section) 53. If an input indicating that image data is to be additionally added is received by the input device 53, the main controller 51 may proceed with the acquisition of image data from the same region of the sample S.

In a sample, for example, there may be factors that are actually difficult to predict, such as degradation or photochemical fading of fluorescent molecules that label biomolecules. With this modification, the user determines whether or not image data is to be additionally added based on an actual raw image, so that a user-friendly raw image that is more appropriate for the sample S can be acquired.

Second Embodiment

Next, a sample observation apparatus and a method for generating an observation image of a sample according to a second embodiment of the present invention will be described.

Figure 7:
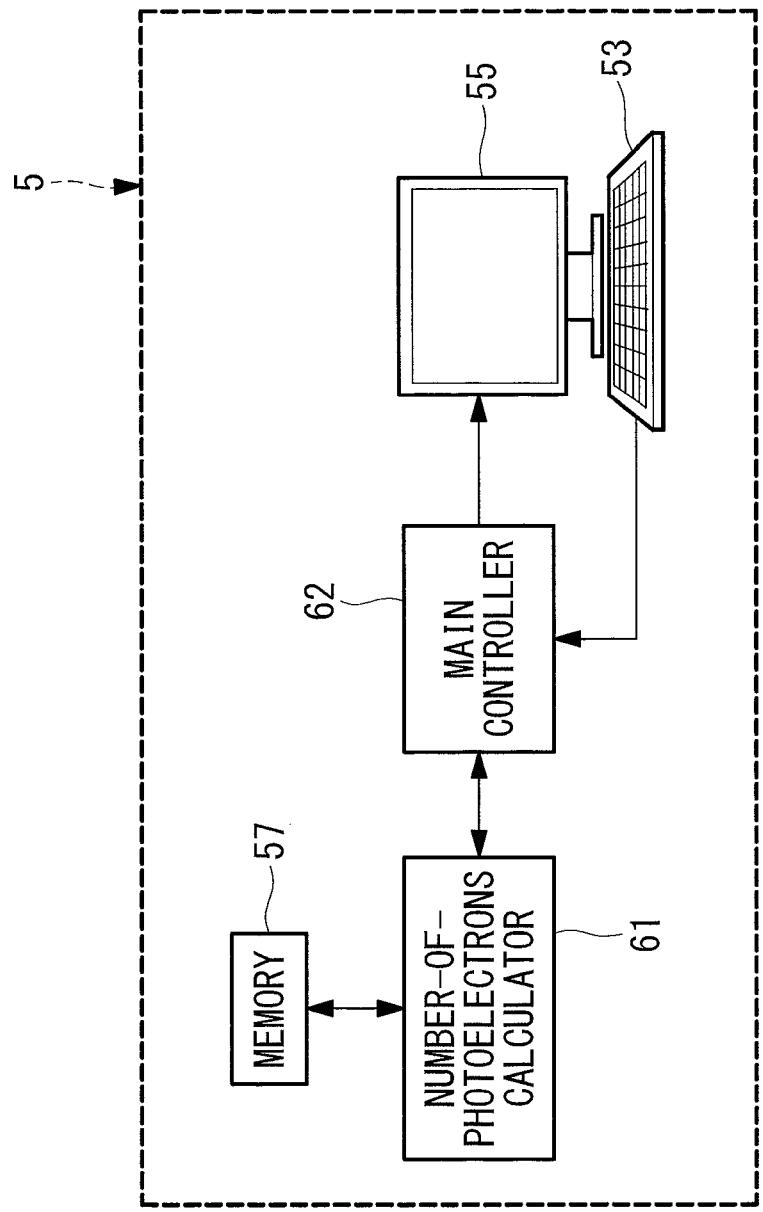
FIG. 7 schematically illustrates the configuration of a system control PC of a sample observation apparatus according to a second embodiment of the present invention.

As shown in FIG. 7, a sample observation apparatus 1 according to this embodiment differs from the first embodiment in that it includes, in place of the main controller 51, a number-of-photoelectrons calculator (S/N-ratio information calculator) 61 that calculates the number of photoelectrons to be acquired in multiple sets of image data to be added together for generating a raw image, and a main controller (image-data acquisition section, condition setting section, controller, raw-image generator) 62 that, for example, sets image acquisition conditions.

Sections similar to those in the sample observation apparatus 1 and the method for generating an observation image of a sample according to the first embodiment will be given the same reference signs, and descriptions thereof will be omitted.

The first number of photoelectrons (first S/N-ratio information) per pixel required for obtaining a desired S/N ratio in a raw image is preliminarily stored as an apparatus parameter A in the memory 57, and an image acquisition time required or advantageous for acquiring a super-resolution image in accordance with the relationship with the time during which the state of the sample S is stable and an experimental program is preliminarily stored as an apparatus parameter T in the memory 57.

As an apparatus parameter P, the number-of-photoelectrons calculator 61 calculates the number of photoelectrons (second S/N-ratio information) per pixel to be acquired in multiple sets of image data to be added together for generating a raw image based on the first number of photoelectrons and the predetermined image acquisition time stored in the memory 57. This number of photoelectrons will be referred to as "second number of photoelectrons" hereinafter.

Specifically, the number-of-photoelectrons calculator 61 multiplies the image acquisition time (apparatus parameter T) stored in the memory 57 by a frame rate (frames/second) so as to calculate the number of repetitions N. Moreover, the number-of-photoelectrons calculator 61 divides the first number of photoelectrons stored in the memory 57 by the number of repetitions N so as to calculate the second number of photoelectrons.

The main controller 62, for example, sets the scanning conditions of the scanner 13, sets the aperture diameter of the diaphragm 25, inserts or removes the optical-path switching mirror 27, sets the amplification gain of the first amplifier 35 and the second amplifier 45, and sets the HV of the first HV power supply 33 and the second HV power supply 43.

Furthermore, the main controller 62 controls the scanner 13 and also acquires image data of the sample S by converting a light intensity signal transmitted from the first amplifier 35 or the second amplifier 45 into luminance information for each pixel corresponding to the scan position of the scanner 13. Moreover, the main controller 62 displays the acquired image data on the monitor 55.

Furthermore, the main controller 62 sets image acquisition conditions for acquiring image data that satisfies the second number of photoelectrons (apparatus parameter P) calculated by the number-of-photoelectrons calculator 61. Specifically, the main controller 62 adjusts the HV multiplication gain of the multi-alkali PMT 31 and the GaAsP-PMT 41, the current-voltage (I-V) conversion characteristics of detection circuits, and the gain of the light-intensity-signal amplifiers (or analog integrating circuits) so that desired luminance (e.g., a maximum value or an intermediate value of a dynamic range) is obtained when the number of photoelectrons (third number of photoelectrons) per pixel in image data to be acquired satisfies the second number of photoelectrons. Moreover, the main controller 62 adjusts the laser light intensity of the light source if a light intensity signal obtained in accordance with the aforementioned image acquisition conditions is excessive or deficient.

Furthermore, the main controller 62 uses the scanner 13 and the detection units 30 and 40 to repeatedly detect the fluorescence from the same region of the sample S for the number of repetitions N calculated by the number-of-photoelectrons calculator 61 so as to acquire image data of the same region. For example, the main controller 62 uses the higher-speed galvanometer mirror of the scanner 13 to scan the excitation laser light N times along the same scan line in the main scanning direction and then swivels the lower-speed galvanometer mirror so as to repeat the operation for moving the scan line in the main scanning direction to the next scan line, thereby acquiring N times worth of image data for every single scan line.

Furthermore, the main controller 62 adds together the N times worth of image data acquired from every single region of the sample S so as to generate the raw image. Then, the main controller 62 applies a filter that emphasizes high-frequency components to the generated raw image so as to generate a super-resolution image that exceeds the optical resolution.

In the method for generating an observation image of a sample according to this embodiment, the main controller 62 causes the number-of-photoelectrons calculator 61 to determine the apparatus parameter P that the image data acquired by the main controller 62 should have (information that the image data should have) based on a preset image acquisition time and the apparatus parameter A stored in the memory 57. Then, image acquisition conditions for acquiring image data that satisfies the apparatus parameter P determined by the number-of-photoelectrons calculator 61 are set in the main controller 62, and the main controller 62 is made to execute control for repeatedly acquiring image data of the same region of the sample S within the image acquisition time. The control executed by the main controller 62 for making the memory 57 store the apparatus parameter A and the process executed by the main controller 62 for generating a raw image are similar to those in the first embodiment.

Figure 8:
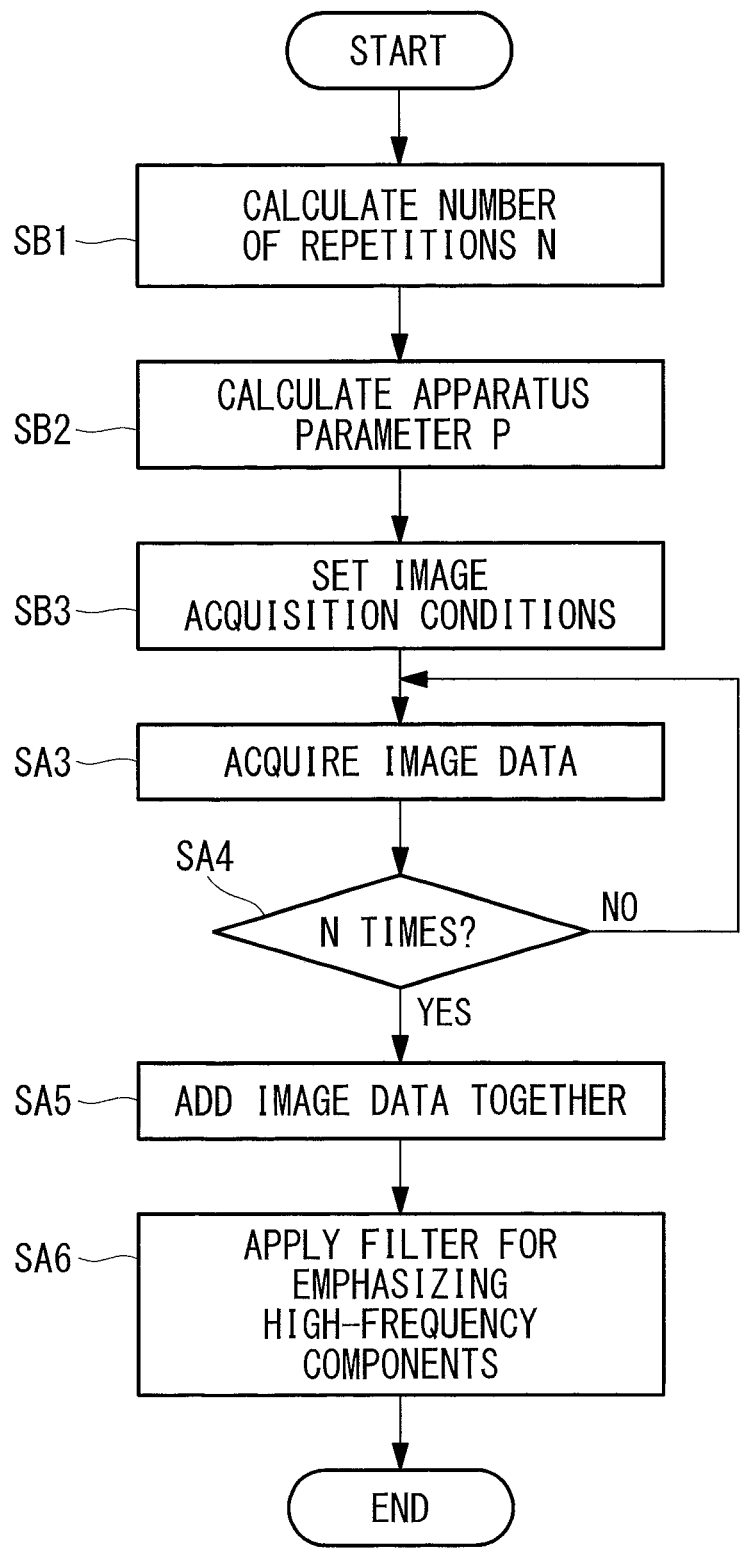
FIG. 8 is a flowchart illustrating a process performed by the sample observation apparatus in FIG. 7 for generating a super-resolution image.

The operation of the sample observation apparatus 1 having this configuration and the method for generating an observation image of a sample will now be described with reference to a flowchart in FIG. 8.

Because the method for acquiring image data of the sample S by using the multi-alkali PMT 31 and the GaAsP-PMT 41 is similar to that in the first embodiment, a description thereof will be omitted.

When a super-resolution image is to be generated by the sample observation apparatus 1 according to this embodiment, the number of photoelectrons multiplied by the multiplication gain (HV dependency) is first calculated based on the HV multiplication gain serving as a PMT parameter, the amplification gain (or integration gain) serving as a circuit parameter, and a sampling period, and an electric charge (current) per photoelectron and a luminance data increment (average value) per photoelectron are preliminarily determined.

Then, the number-of-photoelectrons calculator 61 multiplies the image acquisition time (apparatus parameter T) stored in the memory 57 by the frame rate (frames/second) so as to calculate the number of repetitions N (step SB1).

Subsequently, the number-of-photoelectrons calculator 61 reads the first number of photoelectrons (apparatus parameter A) per pixel required in the raw image from the memory 57, and divides the first number of photoelectrons by the number of repetitions N, so as to calculate the second number of photoelectrons (apparatus parameter P) per pixel to be acquired in each set of image data (step SB2).

Then, the main controller 62 sets image acquisition conditions so that desired luminance (e.g., a maximum value or an intermediate value of a dynamic range) is obtained when the number of photoelectrons (third number of photoelectrons) per pixel in image data to be acquired satisfies the second number of photoelectrons (step SB3).

Since the acquisition of image data (step SA3), the determination of whether or not the number of repetitions N is satisfied ("YES" in step SA4), the addition of image data (step SA5), and the application of the filter that emphasizes high-frequency components are similar to those in the first embodiment, descriptions thereof will be omitted below.

In this case, if the number of times image data of the same region is repeatedly acquired is limited in accordance with the state of the sample S and the experimental program, the image acquisition conditions have to be adjusted in order to ensure a sufficient S/N ratio.

In the sample observation apparatus 1 and the method for generating an observation image of a sample according to this embodiment, the number-of-photoelectrons calculator 61 calculates the second number of photoelectrons (apparatus parameter P) to be acquired in each set of image data obtained within a predetermined image acquisition time for generating a raw image, and the main controller 62 sets image acquisition conditions for acquiring image data that satisfies the second number of photoelectrons, so that the image acquisition conditions required when the image acquisition time is limited can be readily ascertained. Consequently, a good super-resolution image can be generated, while eliminating a troublesome task necessary for generating a raw image.

In this embodiment, the main controller 62 acquires image data, sets the image acquisition conditions, acquires multiple sets of image data from the same region of the sample S, and adds together the multiple sets of image data. Alternatively, for example, the system control PC 5 may include an image-data acquisition section that acquires image data, a condition setting section that sets the image acquisition conditions, a controller that causes the image-data acquisition section to acquire multiple sets of image data from the same region of the sample S, and an image-data adding section that adds together the multiple sets of image data of the same region.

Furthermore, in this embodiment, the main controller 62 may automatically adjust the image acquisition conditions, or may display a warning or an adjustment instruction from the system control PC 5 on the monitor 55 and allow the user to adjust the image acquisition conditions.

Third Embodiment

Next, a sample observation apparatus and a method for generating an observation image of a sample according to a third embodiment of the present invention will be described.

Figure 9:
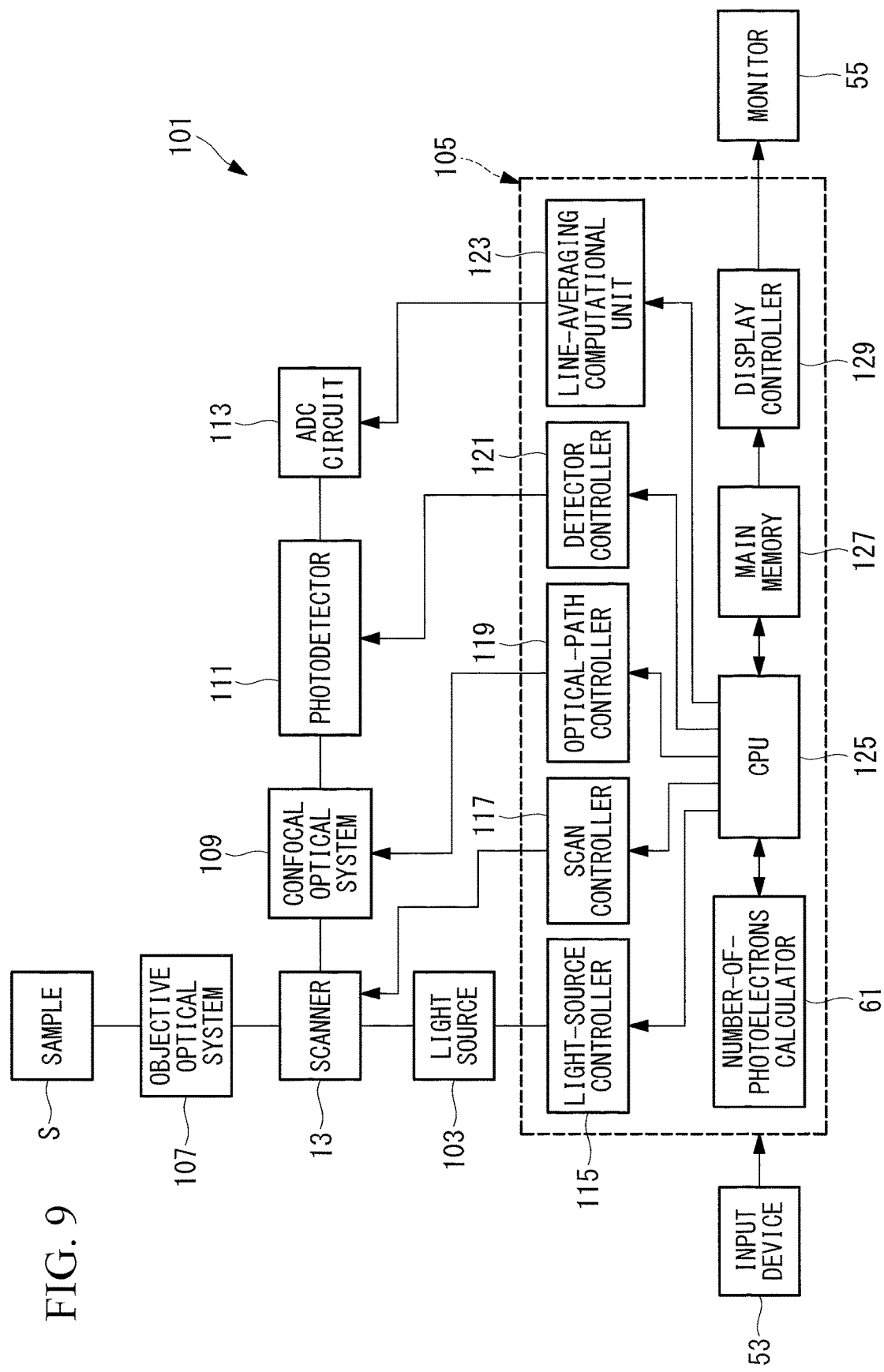
FIG. 9 schematically illustrates the configuration of a sample observation apparatus according to a third embodiment of the present invention.

As shown in FIG. 9, a sample observation apparatus 101 according to this embodiment is a confocal laser scanning microscope and differs from the first embodiment and the second embodiment in that it includes, in place of the system control PC 5, a control device (condition setting section) 105, such as a PC (personal computer), which changes the number of image data sets to be added together in accordance with a mode selected by the user, or a PSU (power supply unit).

Sections similar to those in the sample observation apparatus 1 and the method for generating an observation image of a sample according to each of the first embodiment and the second embodiment will be assigned the same reference signs, and descriptions thereof will be omitted.

The sample observation apparatus 101 includes a light source 103 that generates excitation laser light; a scanner 13; an objective optical system 107; a confocal optical system 109 including, for example, an imaging lens that images fluorescence de-scanned by the scanner 13 and a pinhole that limits the beam of the fluorescence; a photodetector (image-data acquisition section) 111 such as a photomultiplier tube that detects the fluorescence; an ADC (analog-to-digital converter) circuit 113 that converts a light intensity signal output from the photodetector 111 into luminance data (image data); a control device 105; a monitor 55; and an input device 53.

The control device 105 includes a light-source controller 115 that controls the light source 103, a scan controller 117 that controls the scanner 13, an optical-path controller 119 that controls the confocal optical system 109, a detector controller 121 that controls the photodetector 111, a line-averaging computational unit (raw-image generator) 123 that averages a predetermined number of scan lines worth of luminance data, a CPU (central processing unit, controller, raw-image generator) 125 that controls these controllers, a number-of-photoelectrons calculator (S/N-ratio information calculator) 61, a main memory (storage section) 127 that accumulates the averaged luminance data, a display controller 129 that controls the monitor 55, and a line buffer memory (not shown) that accumulates luminance data corresponding to the number of scan lines equivalent to the number of averaging processes.

The control device 105 can select or set image acquisition conditions by allowing the user to operate a GUI (graphic user interface, condition setting section) displayed on the monitor 55 via the input device 53.

Furthermore, by being controlled by software, the control device 105 can acquire a raw image by allowing the user to select a one-shot scan mode in which an image is acquired by scanning excitation laser light only once in X-Y coordinates constituting the image and a line-average scan mode in which an averaging process is performed after repeatedly scanning excitation laser light along the same scan line.

The software has a GUI for switching between a "super-resolution-scan enabled mode" for acquiring a super-resolution image and a "super-resolution-scan disabled mode" for not acquiring a super-resolution image. Furthermore, the software has a GUI to be used when a super-resolution scan is to be performed. The GUI is used for switching between a "speed priority mode", in which the user can select an image processing algorithm suitable for acquiring a super-resolution image with a low S/N ratio and an S/N ratio of a raw image to which the image processing algorithm can be appropriately applied, and an "image-quality priority mode", in which the user can select an image processing algorithm suitable for acquiring a super-resolution image with a high S/N ratio and an S/N ratio of a raw image to which the image processing algorithm can be appropriately applied. In the "speed priority mode", a super-resolution image can be acquired within a shorter period of time. In the "image-quality priority mode", a higher-quality super-resolution image can be acquired by spending more time.

The CPU 125 sets conditions for the light source 103, the scanner 13, the confocal optical system 109, and the photodetector 111 in the light-source controller 115, the scan controller 117, the optical-path controller 119, and the detector controller 121, respectively, in accordance with the image acquisition conditions set by the GUI. Thus, the CPU 125 controls the light source 103, the scanner 13, the confocal optical system 109, and the photodetector 111 via the light-source controller 115, the scan controller 117, the optical-path controller 119, and the detector controller 121, respectively.

The operation of the sample observation apparatus 101 having this configuration will now be described.

In the sample observation apparatus 101 according to this embodiment, excitation laser light emitted from the light source 103 is scanned on the sample S by the scanner 13 via the objective optical system 107. Fluorescence generated in the sample S is collected by the objective optical system 107, is de-scanned by the scanner 13, and is detected by the photodetector 111 via the confocal optical system 109. A light intensity signal output from the photodetector 111 is digitized by the ADC circuit 113 and is transmitted as luminance data to the control device 105.

In the control device 105, the CPU 125 and the line-averaging computational unit 123 average a predetermined number of scan lines worth of luminance data and store the averaged luminance data in the main memory 127. The luminance data stored in the main memory 127 is displayed as an image on the monitor 55 by the display controller 129.

Figure 10:
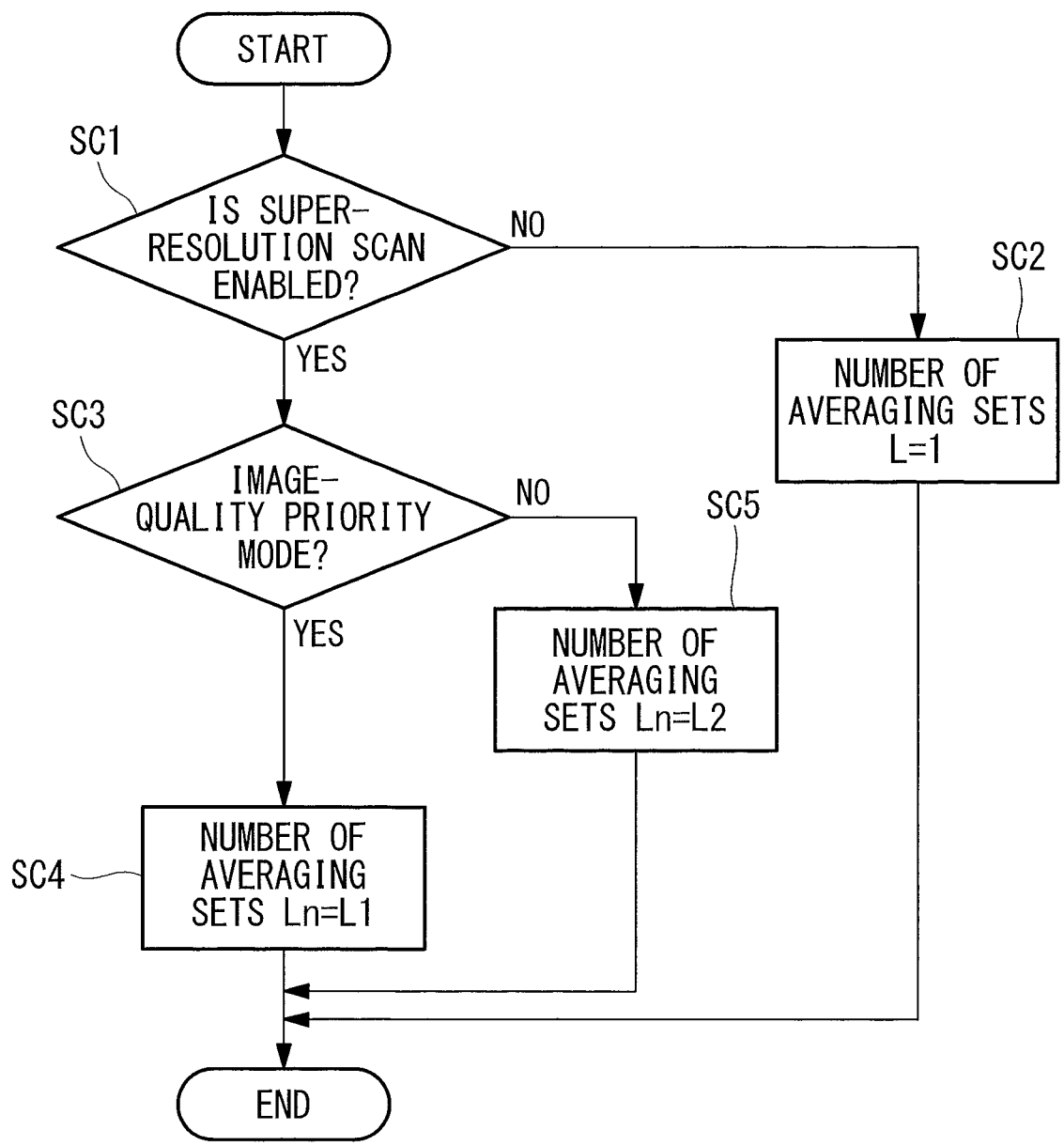
FIG. 10 is a flowchart illustrating a process performed by the sample observation apparatus in FIG. 9 for generating a super-resolution image.

Next, a super-resolution-image acquisition process performed by the sample observation apparatus 101 according to this embodiment will be described with reference to a flowchart in FIG. 10.

First, if the "super-resolution-scan disabled mode" ("NO" in step SC1) is set in the application software in the control device 105, line averaging is not performed (step SC2, the number of averaging sets L=1), and frame image data is generated and is displayed on the monitor 55.

In contrast, if the "super-resolution-scan enabled mode" ("YES" in step SC1) is set in the application software, two separate modes, namely, the "image-quality priority mode" and the "speed priority mode", are provided. If the "image-quality priority mode" is designated ("YES" in step SC3), the number of averaging scan lines Ln is set to L1, and luminance data sets are averaged while repeatedly scanning along every single scan line L1 times (step SC4). Then, frame image data is generated, and the CPU 125 performs a super-resolution filter computational process to generate a super-resolution image in which super-resolution components are visualized and displays the generated super-resolution image on the monitor 55.

In contrast, if the "speed priority mode" is designated ("NO" in step SC3), the number of averaging scan lines Ln is set to L2, and luminance data sets are averaged while repeatedly scanning along every single scan line L2 times (step SC5). In this case, L2<L1. Since the remaining procedure is the same as that in the "image-quality priority mode", a description thereof will be omitted.

In the sample observation apparatus 101 and the method for generating an observation image of a sample according to this embodiment described above, the user does not need to search for or be conscious of the number of averaging scan lines, such as numerical values L1 and L2 shown in the table in FIG. 11, required for obtaining a raw image with image quality suitable for super-resolution processing, and can simply adjust the image exposure based on the laser power and the detector HV and select a super-resolution-image acquisition mode so as to acquire image data in appropriate conditions, whereby a super-resolution image can be easily obtained. In FIG. 11, each laser intensity (Laser) field has an upper section that indicates the number of averaging scan lines L1 corresponding to the image-quality priority mode and a lower section that indicates the number of averaging scan lines L2 corresponding to the speed priority mode.

Furthermore, the conditions for acquiring a super-resolution image are not limited to one pattern. By preparing options like "speed priority" and "image-quality priority", the conditions used for acquiring a super-resolution image can be adjusted in accordance with the time that can be spent on that experiment by the user or whether or not the user desires to take into account fading or photo-toxicity.

The numbers of averaging scan lines L1 and L2 may alternatively be preset fixed values instead of being manipulated and set by the user, and may be set in accordance with the intensity of excitation laser light and the gain of the photodetector 111.

The relationship that the intensity of excitation laser light and the gain of the photodetector 111 have with the numbers of averaging scan lines L1 and L2 may be stored as data in the form of a table or may be defined by, for example, a function formula based on power designated in aW and an HV voltage value that determines the multiplication factor of the photodetector 111.

In this embodiment, only the number of image data sets to be averaged is changed in accordance with the "speed priority mode" or the "image-quality priority mode" selected by the user. Alternatively, for each of the remaining image-acquisition-related parameters, specifically, the image processing algorithm of the filter that emphasizes high-frequency components of a raw image, the detection gain of the GaAsP-PMT 41, the intensity of excitation laser light, the image-data acquisition method, and/or the image-data adding method, a single option or multiple options may be prepared, and the user may select and combine the parameters in accordance with the purpose of the experiment.

Furthermore, multiple combinations of the image processing algorithm of the filter that emphasizes high-frequency components in a raw image, the detection gain of the photodetector 111, the intensity of excitation laser light, the image-data acquisition method, and/or the image-data adding method may be prepared, and the user may select any one of the combinations in accordance with the purpose of the experiment.

In this case, for example, in a filter process performed on a raw image with a small number of averaging scan lines and a relatively low S/N ratio, better image acquisition conditions can be set with a minimal procedure by selecting preferred conditions with multiple parameters cooperating with one another, such as selecting an image processing algorithm that does not excessively emphasize false high-frequency components caused by noise.

Accordingly, with a simple process performed by the user, which simply involves selecting any one of the preset combinations, a troublesome task necessary for generating a raw image can be eliminated.

Although the embodiments of the present invention have been described above in detail with reference to the drawings, the specific configuration is not limited to these embodiments and includes, for example, design modifications so long as they do not depart from the spirit of the invention. For example, the present invention is not limited to each of the above embodiments and the modification and may be applied to an embodiment in which these embodiments and modification are appropriately combined; it is not limited in particular.

REFERENCE SIGNS LIST 1, 101 sample observation apparatus
51 main controller (image-data acquisition section, number-of-image-data-sets calculator, controller, raw-image generator)
53 input device (input section)
57 memory (storage section)
61 number-of-photoelectrons calculator (S/N-ratio information calculator)
62 main controller (image-data acquisition section, condition setting section, controller, raw-image generator)
111 photodetector (image-data acquisition section)
123 line-averaging computational unit (raw-image generator)
125 CPU (controller, raw-image generator)
127 main memory (storage section)
S sample

The invention claimed is:

1. A sample observation apparatus comprising:
a storage that stores information about a signal-to-noise ratio required in a raw image for generating a super-resolution image;
a scanner that scans laser light generated by a light source two-dimensionally on a sample; and
a hardware processor configured to perform processes comprising:
a number-of-image-data-sets calculating process that calculates a number of image data sets to be added together for generating the raw image based on the signal-to-noise ratio information stored in the storage and a predetermined image acquisition condition;
an image-data acquisition process that acquires image data by detecting light from the sample with the predetermined image acquisition condition;
a control process that controls the image-data acquisition process to acquire multiple sets of the image data of a same region of the sample, from among a plurality of regions of the sample, by controlling the image-data acquisition process to repeatedly detect light from the same region based on the number calculated in the number-of-image-data-sets calculating process;
a raw-image generating process that adds together the multiple sets of the image data of the same region acquired in the image-data acquisition process under control of the control process, so as to generate the raw image, wherein a luminance of the raw image is increased according to the number of the image data sets added together; and
a super-resolution image generating process that applies a filter that emphasizes high-frequency components to the raw image generated in the raw-image generating process, so as to generate the super-resolution image,
wherein the control process comprises controlling the scanner to repeatedly scan the laser light along the same region of the sample along a same scan line in a main scanning direction, so as to acquire multiple sets of image data of the same scan line, and to repeat an operation in which, after the scanning is repeatedly performed by the number calculated in the number-of-image-data-sets calculating process in the same scan line in the main scanning direction, the scan line to be repeatedly scanned is changed to a next scan line.

2. The sample observation apparatus according to claim 1, wherein the signal-to-noise ratio information includes a first number of photoelectrons, which is a number of photoelectrons per pixel required for obtaining a desired signal-to-noise ratio in the raw image, and
wherein the number-of-image-data-sets calculating process divides the first number of photoelectrons by a second number of photoelectrons, which is a number of photoelectrons per pixel in the image data acquired with the predetermined image acquisition condition in the image-data acquisition process.

3. The sample observation apparatus according to claim 1, further comprising:
an input device that allows a user to input whether or not to additionally add the image data based on the raw image generated in the raw-image generating process,
wherein when an input indicating that the image data is to be additionally added is received by the input device, the control process controls the image-data acquisition process to continue acquiring the image data for the same region of the sample.

4. A method for generating an observation image of a sample, the method being executed by a hardware processor configured to perform processes including controlling an image-data acquisition process, which acquires image data by detecting light from the sample, to repeatedly acquire image data of a same region of the sample multiple times, from among a plurality of regions of the sample, generating a raw image for creating a super-resolution image of the sample by adding together multiple sets of the image data of the same region repeatedly acquired in the image-data acquisition process as a result of the controlling, and generating the super-resolution image by applying a filter than emphasizes high-frequency components to the raw image, the method comprising:
storing predetermined information related to a signal-to-noise ratio that the raw image should have;
executing one of (i) control for determining a number of image data sets to be added together for generating the raw image based on a preset image acquisition condition for the image-data acquisition process and the stored predetermined information related to the signal-to-noise ratio, and repeatedly acquiring the image data of the same region in accordance with the determined number, and (ii) control for determining information related to a signal-to-noise ratio that the image data acquired in the image-data acquisition process should have based on a preset image acquisition time and the stored predetermined information related to the signal-to-noise ratio, and controlling the image-data acquisition process to repeatedly acquire the image data of the same region within the preset image acquisition time in a state where the preset image acquisition condition for acquiring the image data, which satisfies the determined information related to the signal-to-noise ratio, is set for performing the image-data acquisition process;
generating the raw image by adding together multiple sets of the image data of the same region acquired in the image-data acquisition process as a result of the control executed in the executing, wherein a luminance of the raw image is increased according to the number of the image data sets added together in the generating; and
generating the super-resolution image by applying a filter that emphasizes high-frequency components to the raw image,
wherein the control executed in the executing comprises controlling to repeatedly scan laser light generated by a light source two-dimensionally on the sample, along the same region of the sample, along a same scan line in a main scanning direction, so as to acquire multiple sets of image data of the same scan line, and to repeat an operation in which, after the scanning is repeatedly performed a calculated number of times in the same scan line in the main scanning direction, the scan line to be repeatedly scanned is changed to a next scan line.

* * * * *